(12) United States Patent
Pelerin

(10) Patent No.: US 8,186,356 B2
(45) Date of Patent: May 29, 2012

(54) MOUTH GUARD

(75) Inventor: Joseph Pelerin, Clarkston, MI (US)

(73) Assignee: Dr. Joseph Pelerin, Lake Orion, MI (US)

( * ) Notice: Subject to any disclaimer, the term of this patent is extended or adjusted under 35 U.S.C. 154(b) by 41 days.

(21) Appl. No.: 12/874,281

(22) Filed: Sep. 2, 2010

(65) Prior Publication Data
US 2010/0326451 A1    Dec. 30, 2010

Related U.S. Application Data

(63) Continuation-in-part of application No. 12/558,779, filed on Sep. 14, 2009, now abandoned, which is a continuation-in-part of application No. 11/624,301, filed on Jan. 18, 2007, now Pat. No. 7,607,438.

(60) Provisional application No. 60/761,890, filed on Jan. 25, 2006, provisional application No. 60/825,276, filed on Sep. 12, 2006.

(51) Int. Cl.
A61C 5/14 (2006.01)

(52) U.S. Cl. .............................. 128/859; 128/861; 433/6

(58) Field of Classification Search .................. 128/848, 128/859–962; 433/6
See application file for complete search history.

(56) References Cited

U.S. PATENT DOCUMENTS

| | | | |
|---|---|---|---|
| 3,236,235 A | 2/1966 | Jacobs | |
| 4,689,010 A * | 8/1987 | Wolfe | 433/38 |
| 5,033,480 A | 7/1991 | Wiley et al. | |
| 5,085,584 A | 2/1992 | Boyd | |
| 5,277,203 A | 1/1994 | Hays | |
| 5,316,474 A * | 5/1994 | Robertson | 433/38 |
| 5,460,527 A * | 10/1995 | Kittelsen | 433/215 |
| 5,513,656 A | 5/1996 | Boyd, Sr. | |
| 5,566,684 A | 10/1996 | Wagner | |
| 5,795,150 A | 8/1998 | Boyd | |
| 5,807,100 A * | 9/1998 | Thornton | 433/48 |
| 5,865,619 A | 2/1999 | Cross, III et al. | |
| 6,227,852 B1 | 5/2001 | Schedler et al. | |
| 6,626,180 B1 | 9/2003 | Kittelsen et al. | |
| 6,666,212 B2 | 12/2003 | Boyd, Sr. | |
| 6,749,428 B2 * | 6/2004 | DiMarino et al. | 433/38 |
| 7,234,467 B2 | 6/2007 | Ball | |
| 2004/0144393 A1 | 7/2004 | Conklin | |
| 2004/0241606 A1 | 12/2004 | Diesso | |

FOREIGN PATENT DOCUMENTS

| | | |
|---|---|---|
| JP | 11-42311 A | 6/1989 |
| JP | 3-244480 A | 10/1991 |
| JP | 10-295706 A | 11/1998 |
| WO | WO-03/051280 A2 | 6/2003 |

OTHER PUBLICATIONS

"The Doctor's Night guard-Dental protector for Night Time Teeth Grinding", 2004 Dental Concepts, Paramus, NY 07652. "Bite Soft Anterior Splint", Trident Dental Laboratories, Advertisement, ADA News, Dec. 11, 2006.

* cited by examiner

Primary Examiner — Patricia Bianco
Assistant Examiner — Keri J Nelson
(74) Attorney, Agent, or Firm — Gifford, Krass, Sprinkle, Anderson & Citkowski, P.C.

(57) ABSTRACT

A mouth guard for a human adult which minimizes or eliminates teeth grinding. The mouth guard includes a tray having an arcuate trough opening at each end and dimensioned to receive at least the bicuspids of the human adult. The tray is constructed of a rigid plastic material. A dental impression material is disposed in the tray so that a portion of the impression material extends outwardly from each end of the tray by an amount sufficient to cover the canines or first bicuspids of the human adult when the tray is positioned over the bicuspids.

5 Claims, 2 Drawing Sheets

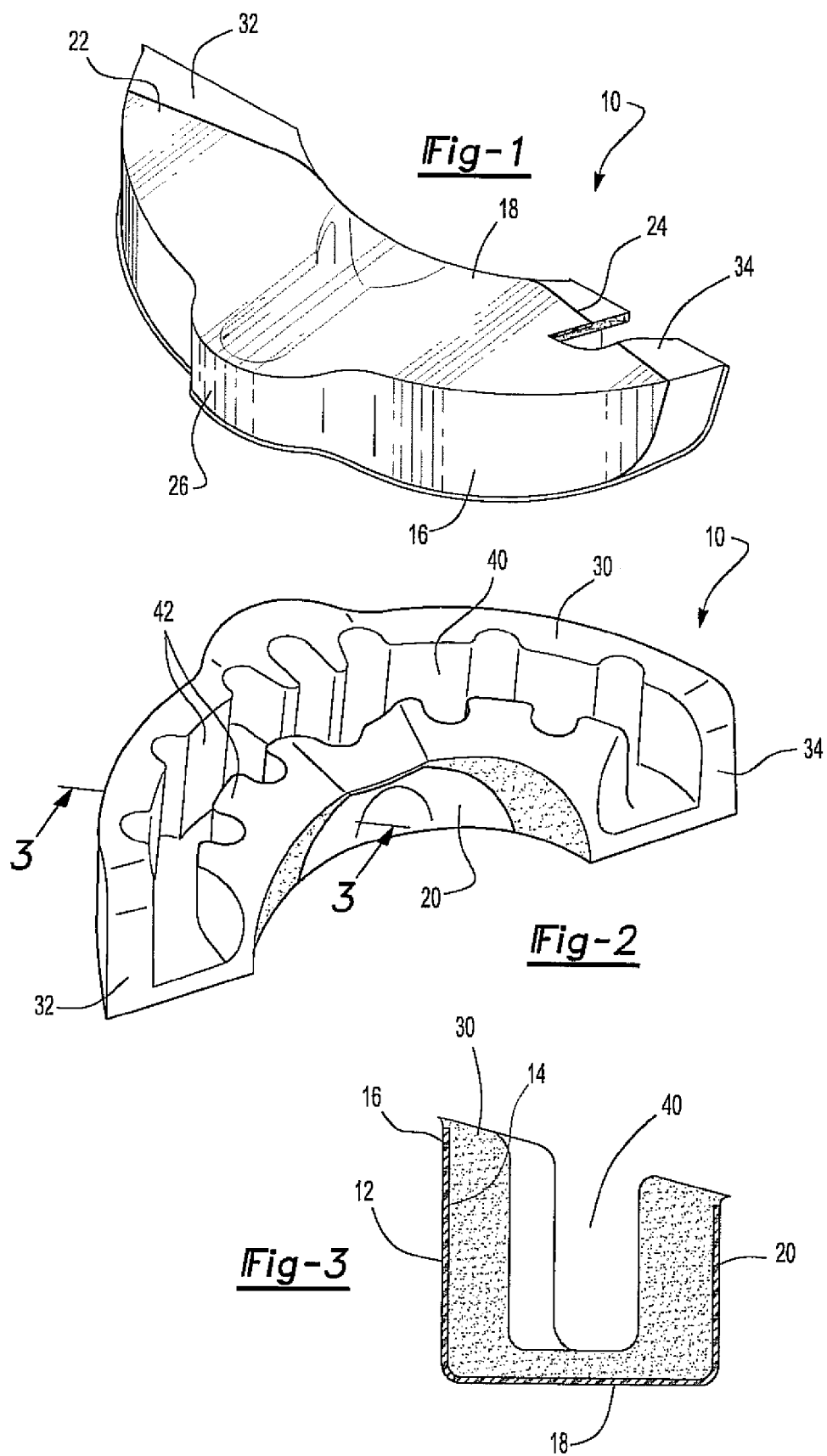

MOUTH GUARD

CROSS REFERENCE TO RELATED APPLICATIONS

This application is a continuation-in-part of U.S. patent application Ser. No. 12/558,779 filed Sep. 14, 2009, which is a continuation-in-part of U.S. patent application Ser. No. 11/624,301 filed Jan. 18, 2007, now U.S. Pat. No. 7,607,438, which claims priority of U.S. Provisional Applications No. 60/761,890 filed Jan. 25, 2006 and No. 60/825,276 filed Sep. 12, 2006.

BACKGROUND OF THE INVENTION

I. Field of the Invention

The present invention relates generally to a mouth guard to minimize teeth grinding during sleep and reduce TMJ and other jaw-related problems.

II. Description of Material Art

Many persons have the tendency of grinding their teeth while sleeping. Such teeth grinding is involuntary and disadvantageously results in undesirable wear of the teeth, TMJ, and other jaw-related problems.

In order to minimize the damage created by the grinding of the teeth, there have been a number of previously known mouth guards which are positioned within the mouth between the teeth on the upper and lower jaws. These previously known mouth guards separate the upper and lower jaws from each other during sleep and thus prevent the teeth from grinding against each other involuntarily during sleep.

The previously known mouth guards, however, have not proven entirely satisfactory in operation. Although the previously known mouth guards effectively eliminate teeth grinding by separating the upper and lower teeth during sleep, they do not eliminate or even significantly reduce involuntary occlusion of the teeth during sleep against the mouth guard. Consequently, while these previously known mouth guards effectively prevent erosion of the teeth caused by grinding during sleep, such guards provide little, if any, relief from temporomandibular joint disease (TMJ) and other jaw-related problems associated with teeth grinding.

A still further disadvantage of these previously known mouth guards is that such mouth guards are typically custom molded to the teeth. As such, they include a full arch tray extending around all of the teeth on the upper or lower jaw. However, the arcuate shape of the mouth of the human adult varies from one adult to the other. For example, in some adults the canines are much more closely spaced together laterally while in other adults the canines are spaced laterally apart from each other by an amount greater than a typical adult human. In these cases, the canines of the human adult do not register with the tray. When this happens, either the tray cannot be used for that particular person, or a modification of the tray by the person is required. Unfortunately, few people are able to correctly modify the mouth guard to fit their own teeth.

SUMMARY OF THE PRESENT INVENTION

The present invention provides a mouth guard which overcomes the above-mentioned disadvantages of the previously known mouth guards.

In brief, the mouth guard of the present invention comprises a partial arch arcuate tray having an arcuate trough open at each end. The tray is dimensioned to receive at least two incisors of a human adult and is constructed of a rigid, but flexible, plastic material.

A dental impression material is disposed in the trough of the tray and extends outwardly from each end of the trough by an amount such that, with the tray positioned over the incisors of a human adult, the outwardly extending amount of the impression material registers with canines or first bicuspids on each side of the incisors of the human adult.

Preferably, the dental impression material is polycapralactone which becomes pliable at an elevated temperature of about 135° Fahrenheit or higher. The impression material, however, sets and retains its shape at a human body temperature of about 100° Fahrenheit.

In order to custom fit the mouth guard to an individual wearer, the tray containing the impression material is first heated to approximately 135° Fahrenheit or higher in any conventional fashion, such as by immersing the tray in hot water. Once the impression material is pliable, the tray is positioned within the wearer's mouth so that the tray extends over the front upper or lower incisors. In doing so, the outwardly extending portion of the dental impression material registers with the person's canines or first bicuspids.

The wearer then occludes into the impression material so that the impression material molds around the person's incisors and canines. The impression material is then allowed to cool and set. Furthermore, once the impression material has set, the impression material frictionally retains the tray in position in the mouth during use.

Consequently, even though the person's canines or first bicuspids do not register with the tray, the canines or first bicuspids register with the outwardly protruding portions of the dental impression material which can be manually manipulated either inwardly or outwardly by the user until such registration is achieved. As a result, the mouth guard may be used by persons having either narrowly spaced or widely spaced canines or bicuspids. Additionally, since the tray is only a partial arch tray, variations in molar size and spacing have no impact on fitting the mouth guard in the patient's mouth.

The tray further preferably includes a mechanism for concentrating the force transmission through the tray caused by occlusion to the area between the upper and lower front incisors. In one form of the invention, a stiffening element is positioned within the tray so that the stiffening element is aligned with the front two incisors of the wearer. The stiffening element thus forms a raised portion in the tray and is less flexible and harder than both the tray and the impression material. Consequently, with the mouth guard positioned in the wearer's mouth, upon occlusion, excess force is transmitted directly to the front incisors.

In yet another embodiment of the invention, the mechanism for concentrating the force transmission through the tray caused by occlusion to the front incisors comprises a thickened area of the tray or a raised portion which is aligned with the front incisors. This raised portion is less flexible and thus harder than the remainder of the tray thereby concentrating the force transmission caused by occlusion to the front incisors.

The concentration of the force transmission caused by occlusion to the front incisors results in an involuntary reflex to open the mouth. Consequently, during sleep an involuntary occlusion concentrates the force of occlusion to the front incisors of the wearer thus helping to stimulate an immediate reflective opening of the mouth. This, in turn, not only prevents teeth grinding, but also may reduce TMJ and other jaw-related problems caused by occlusion or clenching of the teeth during sleep.

BRIEF DESCRIPTION OF THE DRAWING

A better understanding of the present invention will be had upon reference to the following detailed description when read in conjunction with the accompanying drawing, wherein like characters refer to like parts throughout the several views, and in which:

FIG. 1 is an elevational view showing the bottom of the mouth guard of the present invention;

FIG. 2 is an elevational view showing the top of the mouth guard of the present invention;

FIG. 3 is a sectional view taken substantially along line 3-3 in FIG. 2 and enlarged for clarity;

DETAILED DESCRIPTION OF PREFERRED EMBODIMENTS OF THE PRESENT INVENTION

Figure 4:
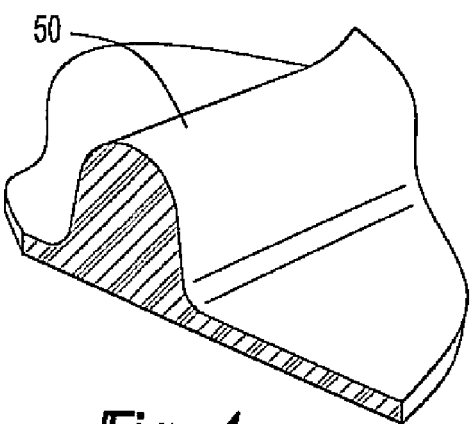
FIG. 4 is a fragmentary elevational view illustrating a front portion of the mouth guard of the present invention and with parts removed for clarity.

With reference first to FIGS. 1-3, a preferred embodiment of a mouth guard 10 according to the present invention is shown. The mouth guard 10 includes an arcuate and thin walled tray 12 thus forming an arcuate trough 14 which is generally U-shaped in cross section. As such, the tray 12 includes a front wall 16, bottom wall 18, and rear wall 20.

The tray 12 is open at each end 22 and 24 and is dimensioned so that the tray extends across at least the front two incisors of an adult human. Furthermore, the tray is constructed of a thin walled, hard but flexible material, such as polyethylene.

The tray 12 also includes a forwardly extending lobe 26 which protrudes outwardly from the front wall 16 of the tray 12. This lobe 26 is generally rounded and located midway between the ends 22 and 24 of the tray. The purpose of the lobe 26 will be subsequently described in greater detail.

Still referring to FIGS. 1-3, a dental impression material 30 is disposed within the tray 12 so that the impression material 30 not only extends between the ends 22 and 24 of the tray 12, but also includes two outwardly protruding portions 32 and 34 which protrude outwardly from the open ends 22 and 24 of the tray 12. These outwardly protruding portions 32 and 34 of the impression material 30 are dimensioned so that, with the tray 12 positioned over the incisors of an adult human, the outwardly protruding portions 32 and 34 at least partially register with the canine or first bicuspid teeth of the adult human.

An arcuate trough 40 is formed through the impression material 30 and extends from one end of the impression material 30 and to the other end of the impression material 30. The impression material 30 also includes a plurality of longitudinally spaced and inwardly extending ridges 42 which extend laterally into the trough 40.

The dental impression material 30 comprises a thermoplastic material which is pliable at an elevated temperature, such as 135° Fahrenheit or higher, and yet sets and retains its shape at the temperature of a human body, i.e. about 100° Fahrenheit. One such material is about 75% by weight of polycaprolactone and about 25% by weight of ethylene co-vinyl acetate. Other materials, such as polyvinyl silicone, may also be used.

With reference now to FIG. 4, the mouth guard 10 of the present invention preferably includes a mechanism for concentrating the force transmission through the tray which is created by occlusion to the area between the upper and lower front incisors. This mechanism may comprise a thickened portion 50 of the tray 12 which is positioned midway around the tray 12 and extends between the rear wall 20 and front wall 16 of the tray 12. Since the raised portion 50 of the tray 12 is much more rigid and harder than the remainder of the tray 12 as well as the impression material 30, the raised portion 50 transmits occlusion force between the incisors of a human adult.

Figure 5:
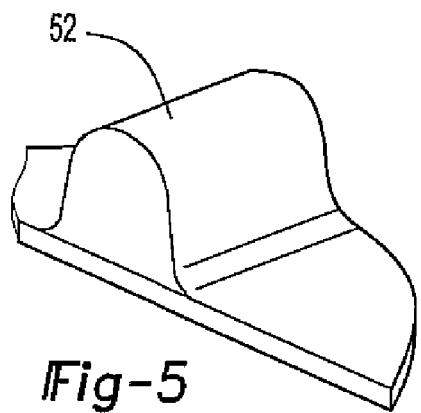
FIG. 5 is a view similar to FIG. 4, but illustrating an alternate embodiment.

With reference now to FIG. 5, an alternative mechanism for concentrating the occlusion force to the person's front two incisors is a separate stiffening element 52 which is mounted within the tray 12. The stiffening element 52 may be constructed of any hard and rigid material and is positioned midway between the ends of the tray 12 and extends between the tray front wall 16 and rear wall 20.

In order to custom fit the mouth guard 10 to the mouth of a human adult, the entire guard is first heated to a temperature in excess of about 135° Fahrenheit. This is easily accomplished by merely submersing the tray with its impression material 30 into hot water. After a minute or so, the impression material 30 becomes soft and pliable.

The mouth guard 10 is then centered over the person's incisors on either the upper or lower jaw such that at least the person's two front incisors 60 register with the trough 40 formed in the impression material 30. In doing so, the ridges 42 formed in the impression material facilitate the easy insertion of the adult human's teeth into the trough 40 and yet maintain sufficient contact between the impression material 30 and the person's teeth to form a good frictional fit between the mouth guard 10 and the person's teeth.

Figure 6:
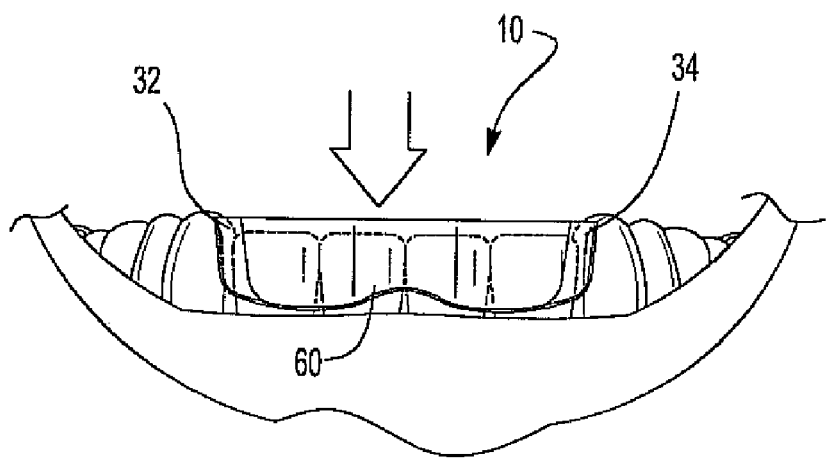
FIG. 6 is a view illustrating the use of the mouth guard.

When the mouth guard 10 is positioned within the person's mouth as shown in FIG. 6, the outwardly extending portions 32 and 34 of the impression material 30 at least partially register with the person's canine or first bicuspid teeth. In the event that the canines or first bicuspids are much more closely spaced together or widely spaced apart from each other than in a typical adult human, the flexible end portions 32 and 34 of the impression material 30 may be easily manipulated by the user so that they register with the canine or first bicuspid teeth depending on the size of the wearer's mouth.

Once the mouth guard 10 is positioned over the teeth as shown in FIG. 6, the user occludes to fully seat the mouth guard 10 and then allows the mouth guard 10 to cool. Upon cooling, the dental impression material 30 retains its molded shape. Consequently, the mouth guard 10 may be removed from the mouth when desired and, upon a subsequent reinsertion of the mouth guard 10, the impression material frictionally retains the mouth guard in place.

In use, the raised portion 50 (FIG. 4) of the tray 12 or the stiffening element 52 (FIG. 5) concentrates the force transmission through the tray caused by occlusion so that the force of the occlusion is transmitted almost entirely to the front upper and lower incisors. This, in turn, causes a reflective opening of the mouth immediately in response to such occlusion, even during sleep. This, in turn, effectively prevents teeth grinding in most cases and reduces or eliminates TMJ and other jaw-related problems which are caused by or aggravated by clenching of the teeth during sleep.

The mouth guard 10 may be used on either the upper or the lower teeth. However, when used on the person's lower teeth, the lobe 26 protrudes forwardly and ensures that the upper incisors will contact the mouth guard upon occlusion.

From the foregoing, it can be seen that the present invention provides a simple yet effective mouth guard for minimizing or altogether preventing teeth grinding during sleep. Having described my invention, however, many modifications thereto will become apparent to those skilled in the art to which it pertains without deviation from the spirit of the invention as defined by the scope of the appended claims.

I claim:

1. A mouth guard for a human adult having bicuspids and canines comprising:
   a tray having an arcuate trough open at each end and dimensioned to receive at least a portion of the incisors of the human adult, said tray constructed of a rigid plastic material,
   dental impression material disposed in said trough of said tray and extending outwardly from each end of said trough by an amount such that, with said tray positioned over the incisors of an adult human, the outwardly extending amount of said impression material registers with canine or first bicuspid teeth of the human adult, an arcuate channel formed in said impression material, said channel extending between the ends of the impression material and having spaced apart inner and outer sidewalls,
   wherein said impression material includes a plurality of longitudinally spaced ridges which extend laterally inwardly into said channel from both said inner and outer sidewalls of said channel at longitudinally spaced positions along said channel.

2. The mouth guard as defined in claim 1 and comprising a raised portion of said tray positioned midway between the ends of said tray.

3. The mouth guard as defined in claim 2 wherein said raised portion and said tray are a one piece construction.

4. The mouth guard as defined in claim 1 wherein said impression material comprises polycapralactone.

5. The mouth guard as defined in claim 1 wherein said tray comprises a forwardly extending lobe positioned midway between the ends of said tray.

* * * * *